United States Patent [19]
Dietz et al.

[11] Patent Number: 5,462,550
[45] Date of Patent: Oct. 31, 1995

[54] ALIGNMENT GUIDE AND METHOD

[75] Inventors: Terry L. Dietz, Columbia City; Stephen C. Miller, Warsaw, both of Ind.

[73] Assignee: Zimmer, Inc., Warsaw, Ind.

[21] Appl. No.: 143,910

[22] Filed: Oct. 27, 1993

Related U.S. Application Data

[63] Continuation of Ser. No. 929,241, Aug. 13, 1992, abandoned.

[51] Int. Cl.⁶ .............................. A61F 5/00; A61B 17/58
[52] U.S. Cl. .................. 606/86; 606/87; 606/88
[58] Field of Search .................. 606/86, 87, 88, 606/89, 96, 97, 98; 407/4; 408/116; 523/16, 18, 20, 23

[56] References Cited

U.S. PATENT DOCUMENTS

| | | | |
|---|---|---|---|
| 4,474,177 | 10/1984 | Whiteside | 606/88 |
| 4,646,729 | 3/1987 | Kenna | 606/88 |
| 4,787,383 | 11/1988 | Kenna | 606/88 |
| 4,791,919 | 12/1988 | Elloy et al. | 128/92 |
| 5,035,700 | 7/1991 | Kenna | 606/88 |
| 5,037,423 | 8/1991 | Kenna | 606/87 |
| 5,100,409 | 3/1992 | Coates | 606/88 |
| 5,171,243 | 12/1992 | Kashuba | 606/86 |
| 5,176,684 | 1/1993 | Ferrante | 606/87 |

*Primary Examiner*—Michael A. Brown
*Attorney, Agent, or Firm*—Cary R. Reeves

[57] ABSTRACT

An alignment guide comprises a guide block locator having surfaces for engaging a prepared femur and establishing a specific position relative to an intercondylar slot in the femur. The guide block locator contains an aperture for directing a guide block to the specific position. The guide block includes a leg that can be driven into the femur to hold the guide block in place. The guide block is adapted to precisely engage the cam box of a femoral implant. Upon removal of the guide block locator, the femoral implant can be positioned over the guide block where the cam box will engage the guide block before the anterior and posterior flanges of the implant grip the anterior and posterior surfaces of the femur thereby providing proper alignment of the femur and implant.

14 Claims, 3 Drawing Sheets

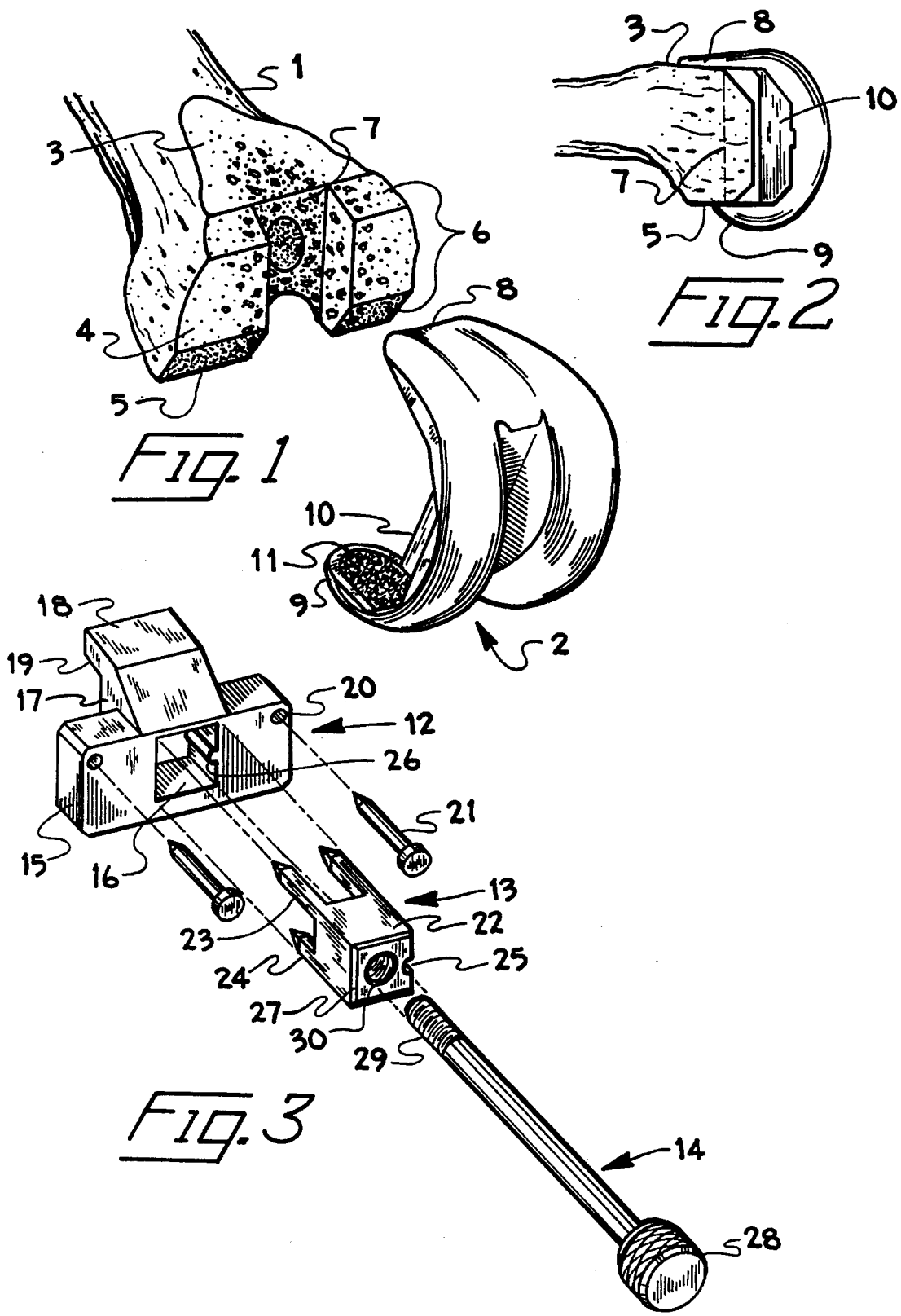

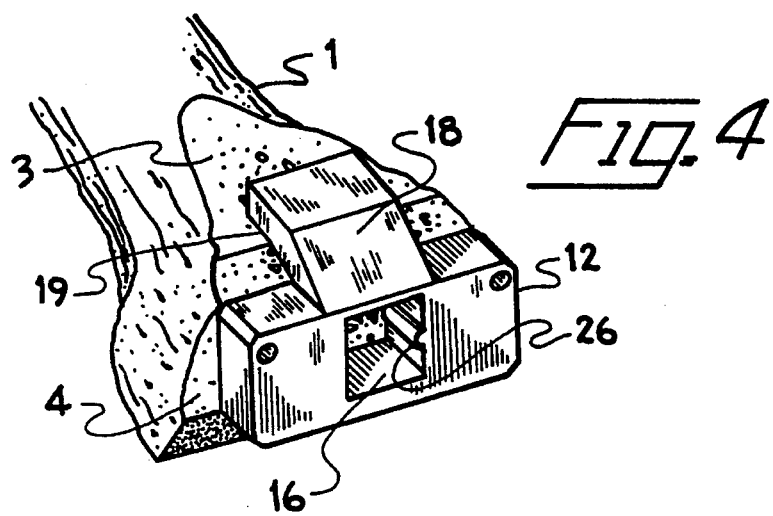
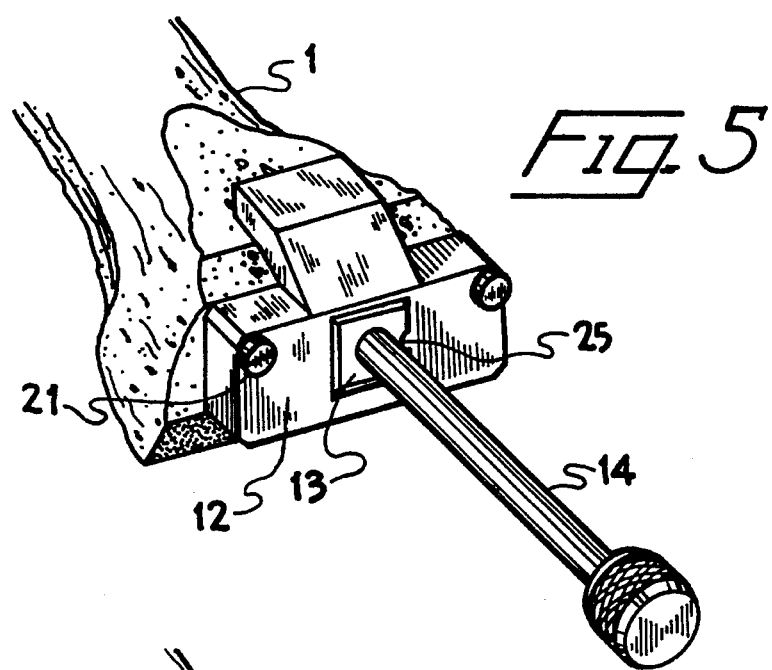
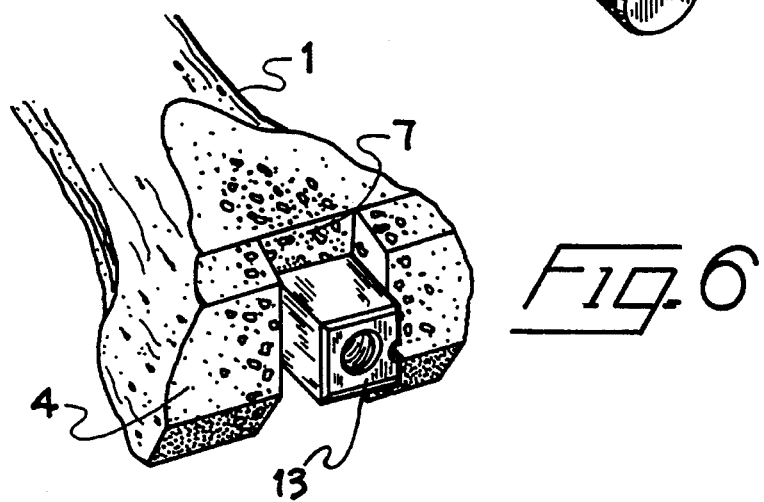

5,462,550

ALIGNMENT GUIDE AND METHOD

This is a continuation of application Ser. No. 07/929,241 filed Aug. 13, 1992, now abandoned.

BACKGROUND OF THE INVENTION

The present invention relates to instruments for aiding in implanting prosthetic implants. More specifically, the present invention relates to an alignment guide to aid in seating a femoral knee implant.

In a typical knee replacement surgery, the end of the femur is prepared to receive a femoral knee implant by resecting bone in anterior, distal, posterior, and chamfer planes. In order to implant a constrained knee having a cam box additional bone must be removed to form a slot in the intercondylar region. After the femur is prepared the femoral implant is pressed onto the femur. As the implant is advanced onto the femur the anterior and posterior flanges of the implant contact the anterior and posterior surfaces of the femur before the cam box engages the slot in the femur. Because of this, the cam box may not be aligned with the slot. If the cam box and slot are not aligned, proper seating of the implant is impossible without repositioning the implant medially or laterally. Repositioning the implant can erode the carefully prepared bone surfaces and thereby compromise a precise fit between the implant and bone.

SUMMARY OF THE INVENTION

The present invention provides an apparatus useful to avoid misalignment between the femoral bone and femoral knee implant. Furthermore, the apparatus is simple to use and serves as a gauge to verify that the bone preparation is complete and accurate before the implant is seated. The alignment guide of the present invention comprises a guide block locator having surfaces for engaging the prepared femur and establishing a specific position relative to the intercondylar slot. The guide block locator contains an aperture for directing a guide block to the specific position. The guide block includes a leg that can be driven into the femur to hold the guide block in place. The guide block is adapted to precisely engage the cam box of the femoral implant. Upon removal of the guide block locator, the femoral implant can be positioned over the guide block where the cam box will engage the guide block before the anterior and posterior flanges of the implant grip the anterior and posterior surfaces of the femur thereby providing proper alignment of the femur and implant. The implant is then fully seated on the bone and the guide block is removed. A detachable handle is provided to facilitate placement and removal of the guide block. In one embodiment, multiple legs of different length hold the guide block in position and the guide block and guide block locator are keyed so that the guide block can only be placed in one preferred orientation.

BRIEF DESCRIPTION OF THE DRAWINGS

FIG. 1 is an exploded perspective view showing a prepared femur and a femoral implant.

FIG. 2 is a side view of the femoral implant of FIG. 1 showing the anterior and posterior flanges engaging the anterior and posterior femoral surfaces before the cam box engages the intercondylar slot.

FIG. 3 is an exploded perspective view showing the components of the alignment guide.

FIG. 4 is a perspective view of a guide block locator positioned on a prepared femur.

FIG. 5 is a perspective view of a guide block, with attached handle, positioned within the guide block locator of FIG. 4.

FIG. 6 is a perspective view of the guide block of FIG. 5 after the guide block locator and handle have been removed.

DETAILED DESCRIPTION OF THE INVENTION

Figure 7:
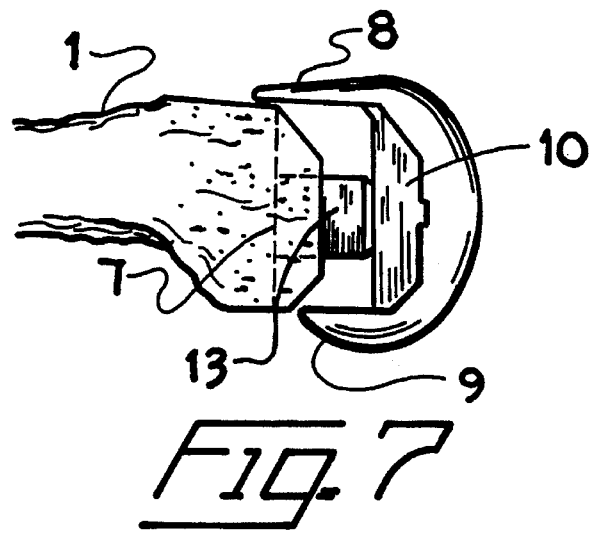
FIG. 7 is a side view showing the cam box engaging the guide block before the anterior and posterior flanges engage the anterior and posterior surfaces.

FIG. 1 depicts an end of a femur 1 prepared to receive a femoral implant 2. The prepared femur has anterior 3, distal 4, posterior 5 and chamfer 6 planar surfaces and a slot 7. The planar surfaces and the slot 7 are sized and positioned to engage the implant 2 in an interference, or press, fit. The implant 2 used in this illustrative example includes an anterior flange 8, typically angled approximately five degrees outwardly, a posterior flange 9, and a box 10. The box 10 in this example houses a cam means for cooperating with a corresponding tibial implant. The femoral implant 2 further includes porous surface material 11 on the anterior 8 and posterior 9 flanges. During the implantation of this type of implant, it is necessary for the box 10 to be aligned, especially medially and laterally, with the slot 7 in order for the implant 2 to seat fully on the femur 1. However, it is seen in FIG. 2 that the anterior flange 8 and the posterior flange 9 engage the anterior 3 and posterior 5 surfaces of the femur before the box 10 engages the slot 7. Because of this, misalignment of the box 10 and slot 7 can occur. Because of the interference fit between the implant and bone such misalignment is difficult to correct without removing the implant and beginning the implantation again. Placing and replacing the implant may erode the bone enough to compromise the interference fit desired.

An alignment guide, according to the present invention, is shown in FIG. 3. The alignment guide includes a guide block locator (locator) 12, a guide block 13, and a handle 14. The locator 12 is used to position the guide block 13 within the slot 7. The guide block 13, in turn, is used to position the femoral implant 2. Finally, the handle 14 is used to facilitate placement and removal of the guide block 13. The locator 12 includes a locator body 15 having an aperture 16 for engaging the guide block 13. A lateral surface 17 extends from the body to engage a side of the slot 7 and thereby indicate the proper medial-lateral position for the locator 12. Advantageously a complementary and opposite lateral surface is provided so that the locator closely engages both sides of the slot 7. These lateral surfaces further advantageously approximate the size and shape of the box 10 so that when the locator is placed on the femur it serves to gauge the sufficiency of the slot 7 for receiving the box 10. An extension 18 extends from the locator body 15 and defines an anterior reference surface 19 for positioning the locator with respect to the anterior surface 3 of the femur. The locator also advantageously includes pin holes 20 to accommodate pins 21 for fixing the locator to the femur. Turning now to the guide block 13, it includes a guide block body 22 of regular geometric shape. Legs 23 and 24 extend from the guide block body to fix the guide block on the femur. The anterior legs 23 take advantage of the femoral geometry which allows longer legs anteriorly for better fixation. The posterior legs 24 are shorter to minimize the chance of them perforating the posterior side of the femur above the condyles. Because of the difference in leg length, it is advantageous to provide a keyway 25 on the guide block and a key 26 in the aperture 16 so that the guide block must be properly oriented in the locator. The guide block body 22 is shaped to closely engage the box 10 of the implant 2 so that the implant is precisely positioned when it is placed over the guide block body. To facilitate placement of the implant 2 over the guide block body 22, the guide block body is preferably chamfered 27. A handle 14 is provided to facilitate placement and removal of the guide block 13. The handle has a knob 28 which can be struck with a mallet to drive the guide block legs 23 and 24 into the femur and which can engage a slap hammer for removal of the guide block. A threaded end 29 of the handle and a corresponding threaded hole 30 in the guide block 13 provide a means for attaching the handle to the guide block.

Figure 8:
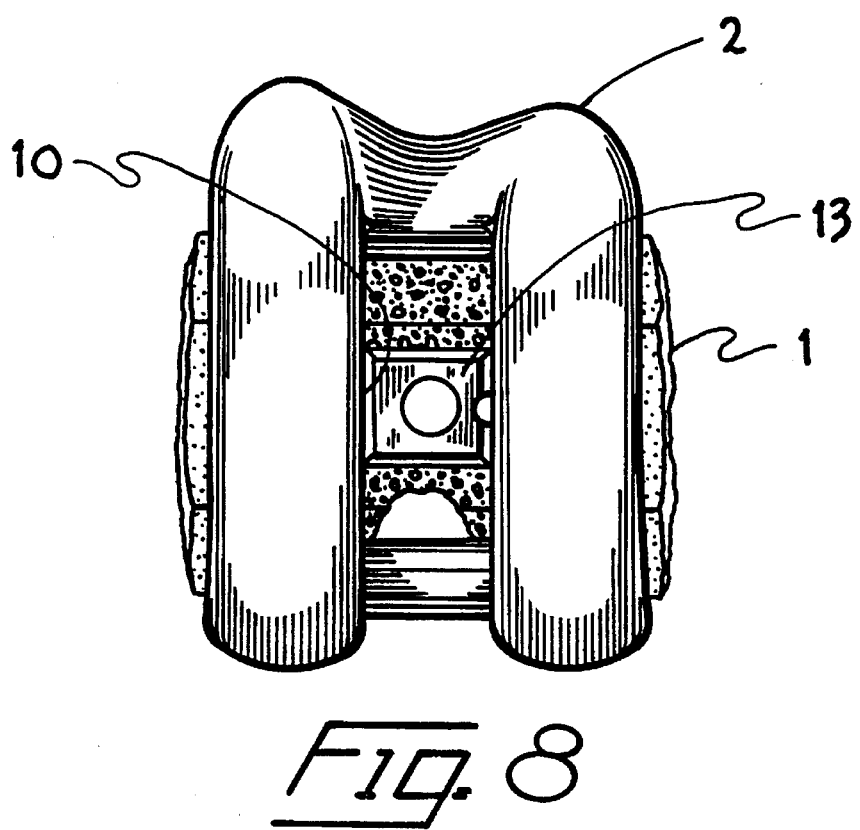
FIG. 8 is a plan view of a femoral implant seated on the femur and engaging the guide block.

In use the locator 12 is placed against the distal surface 4 of the prepared femur 1 with the lateral surface 17 adjacent the side of the slot 7 and the anterior reference surface 19 of the extension 18 adjacent the anterior surface 3 of the femur as shown in FIG. 4. If the locator is made to approximate the relationship between the implant and box as described above, it will indicate, by not fully seating, whether the slot requires more bone resection. If further resection is required, the locator is removed, the resection is performed, and the locator is replaced on the femur. Now, pins 21 are placed in pin holes 20 and driven into the femur to hold the locator 12 in place. The guide block 13, with handle 14 attached, is then oriented so that keyway 25 aligns with key 26 and the guide block is placed in the aperture 16 as shown in FIG. 5. The guide block 13 is driven via the handle 14 until legs 23 and 24 are fully seated. The handle 14, pins 21 and locator 12 are removed so that the guide block 13 remains in the slot 7 and protrudes beyond the distal surface 4 as shown in FIG. 6. With the guide block 13 protruding, the box 10 will now engage the guide block 13, as shown in FIG. 7, before the anterior 8 and posterior 9 flanges of the implant grip the bone. Note that when the box begins to engage the guide block, the flanges will begin to extend over the bone but because of the outward angle of the anterior flange, the flanges will not yet grip the bone. In this way, alignment of the box 10 with the slot 7 is assured. The implant 2 is then fully seated on the femur. FIG. 8 shows the close engagement medially and laterally between the guide block 13 and the box 10. The ability of a surgeon to sight through the box and along the sides of the guide block further aids implant alignment. Finally, the handle 14 is reattached to the guide block 13 and the guide block is removed.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. An apparatus for aligning a femoral knee implant with a prepared surface of a femur, the apparatus comprising:

a guide means for guiding the femoral knee implant to a desired location on the femur, the guide means being matingly engageable with the implant; and a guide locator means for locating the guide means at a specific location on the femur, the guide locator means being matingly engageable with the guide means.

2. The apparatus of claim 1 wherein the guide locator means locates the guide means in a spaced relationship to a known feature of the femur.

3. The apparatus of claim 2 wherein the guide locator means includes a lateral surface for engaging a side of a slot in the prepared femur.

4. The apparatus of claim 3 wherein the guide locator means includes an anterior reference surface for engaging an anterior surface of the prepared femur.

5. An alignment guide for aligning a femoral knee implant with a prepared femur, the implant having an intercondylar box and the prepared femur having a corresponding intercondylar slot, the alignment guide comprising:

a guide block having a body matingly engageable with the box, a guide block locator having an aperture matingly engageable with the guide block body, the guide block locator being adapted to position the guide block on the femur at a particular location with respect to the slot.

6. The guide of claim 5 wherein the aperture and body are keyed to orient their engagement.

7. The guide of claim 5 further comprising at least one leg extending from the guide block, the leg being adapted to be driven into the femur.

8. The guide of claim 5 further comprising at least one anterior leg extending from the guide block and at least one posterior leg extending from the guide block, the anterior leg being longer than posterior leg.

9. The guide of claim 5 wherein the guide block body has an end for engaging the femur and an end for engaging the implant, the end for engaging the implant being chamfered to aid engagement.

10. The guide of claim 5 further comprising a handle removably engageable with the guide block.

11. The guide of claim 5 wherein the guide block locator includes a lateral surface corresponding to a side of the intercondylar box of the implant.

12. The guide of claim 11 wherein the guide block locator includes an anterior reference surface for engaging an anterior surface of the prepared femur.

13. A method for aligning a femoral knee implant with a prepared femur, the method comprising the steps of:

positioning a guide block locator on the prepared end of the femur;

positioning a guide block with reference to the guide block locator;

removing the guide block locator from the femur;

positioning the implant with respect to the guide block; and removing the guide block.

14. A method for aligning a femoral knee implant with a prepared femur, the implant having an intercondylar box and the prepared femur having a corresponding intercondylar slot, the method comprising the steps of:

positioning a guide block locator on the prepared end of the femur with reference to the slot;

positioning a guide block with reference to the guide block locator by matingly engaging the guide block and guide block locator;

removing the guide block locator from the femur;

positioning the implant with respect to the guide block by matingly engaging the implant and the guide block; and removing the guide block.

\* \* \* \* \*